United States Patent [19]

Posthuma et al.

[11] Patent Number: 5,068,254

[45] Date of Patent: Nov. 26, 1991

[54] PROCESS FOR THE PREPARATION OF HYDROCARBONS

[75] Inventors: Sytze A. Posthuma, The Hague; Johannes D. de Graaf; Jan Boelen, both of Rotterdam/Pernism, all of Netherlands

[73] Assignee: Shell Oil Company, Houston, Tex.

[21] Appl. No.: 520,333

[22] Filed: May 7, 1990

[30] Foreign Application Priority Data

May 15, 1989 [GB] United Kingdom ............... 8911076

[51] Int. Cl.$^5$ .............................................. C07C 1/04
[52] U.S. Cl. ................................................... 518/705
[58] Field of Search ......................................... 518/705

[56] References Cited

U.S. PATENT DOCUMENTS

| | | | |
|---|---|---|---|
| 3,715,195 | 2/1973 | Tassoney et al. | 518/705 |
| 3,957,460 | 5/1976 | Lee | 518/705 |
| 3,966,633 | 6/1976 | Friedman | 518/705 |

OTHER PUBLICATIONS

Quartulli, Hydrocarbon Processing, 1975, pp. 94–99.

*Primary Examiner*—Howard T. Mars
*Attorney, Agent, or Firm*—Ronald R. Reper

[57] ABSTRACT

The invention relates to a process for the preparation of hydrocarbons by a catalytic reaction of a mixture of carbon monoxide and hydrogen, comprising the steps of:

(i) providing a gas mixture comprising carbon monoxide and hydrogen;
(ii) washing the mixture with an aqueous solution for the removal of impurities from the mixture;
(iii) removing the washing solution containing the impurities from the mixture;
(iv) contacting the washed mixture with a catalyst whereby hydrocarbons and reaction water are formed;
(v) separating the reaction water from the hydrocarbons; and
(vi) using reaction water as aqueous solution in washing step (ii)

and to hydrocarbons obtained therewith.

5 Claims, No Drawings

PROCESS FOR THE PREPARATION OF HYDROCARBONS

BACKGROUND OF THE INVENTION

FIELD OF THE INVENTION

The present invention relates to a process for the preparation of hydrocarbons by a catalytic reaction of a mixture of carbon monoxide and hydrogen with a catalyst.

It is known to prepare liquid hydrocarbons by converting a hydrocarbonaceous feed (for instance natural gas) into synthesis gas (a mixture comprising mainly hydrogen and carbon monoxide) and subsequently converting catalytically the synthesis gas into liquid and gaseous hydrocarbons. The catalytic reaction of the mixture of carbon monoxide and hydrogen at elevated temperature and pressure with a catalyst is known in literature as the Fischer-Tropsch hydrocarbon synthesis process.

These Fischer-Tropsch catalysts comprise one or more metals from the iron group together with one or more promotors deposited on a carrier material. More specifically such a catalyst comprises 3-80 parts by weight of cobalt, especially 15-50 parts by weight of cobalt, and 0.1-100 parts by weight of at least one other metal selected from the group consisting of zirconium, titanium, chromium and ruthenium, preferably 5-40 parts by weight of zirconium per 100 parts by weight carrier material. As carrier materials may be exemplified silica, zirconia, alumina or silica-alumina. Preferably silica is used. Suitable techniques for the preparation of these catalysts comprise precipitation, impregnation, kneading and melting. For further information reference is made to EP-A-127,220 and US 4,599,481.

These Fischer-Tropsch catalysts are very sensitive to impurities present in the mixture of carbon monoxide and hydrogen. These impurities, for instance $NH_3$ and HCN, poison the catalyst, resulting in a decrease of the activity and specificity of the catalyst. These poisoning impurities are produced in harmful concentrations in various processes for the formation of the mixture of carbon monoxide and hydrogen, such as steam reforming or partial oxidation of light hydrocarbons, such as natural gas, particularly methane.

The poisoning impurities consist mainly of HCN and $NH_3$. Sulphur containing compounds are usually already removed before the formation of the mixture of carbon monoxide and hydrogen, whereas $NO_x$ only affects the sensitivity of the Fischer-Tropsch catalyst to a minor extent. The removal of HCN and $NH_3$ to concentrations below 1 ppm requires very large amounts of water. Water from a river or lake might be used, but requires a purification treatment. Salty sea water cannot be used.

It is an object of the invention to provide a process for the preparation of hydrocarbons from synthesis gas, comprising carbon monoxide and hydrogen, in which the use of extraneous water and the associated water purification costs are avoided. The invention is based on the insight that the catalytic formation of the hydrocarbons results in the formation of a sufficient amount of reaction water having a sufficient purity, so that this reaction water may be used for the removal of the poisoning impurities from the synthesis gas.

SUMMARY OF THE INVENTION

Therefore, the present invention relates to a process for the preparation of hydrocarbons by a catalytic reaction of a mixture of carbon monoxide and hydrogen, comprising the steps of:
  i) providing a gas mixture comprising carbon monoxide and hydrogen and at least one impurity selected from hydrogen cyanide and ammonia;
  ii) washing said gas mixture with an aqueous solution in a wash zone to obtain a washed gas mixture having a reduced level of impurities and a fat aqueous solution containing impurities from said gas mixture;
  iii) separating said fat aqueous solution from the mixture;
  iv) contacting said washed gas mixture at an elevated temperature and pressure with a catalyst whereby a hydrocarbon-containing reaction product and reaction water are obtained;
  v) separating said reaction water from said hydrocarbon product; and
  vi) recycling at least part of said reaction water as aqueous solution to said wash zone of step (ii).

DESCRIPTION OF PREFERRED EMBODIMENTS

In order to enhance the absorption of the impurities in the aqueous washing solution, this washing solution may comprise chemicals promoting the absorption of the impurities, for instance ferrous sulphate and/or sodium hydroxide. The absorption of the impurities in the wash zone may be further enhanced if the synthesis gas is cooled, for instance from about 100-200° C. to about 15-75° C.

For an optimal flexibility of the process control and the degree of purification, it is preferred that the washing step comprises a first washing step using reaction water and a second washing step using a washing solution comprising the chemicals.

The washing solution containing the impurities might be sent to waste and disposed as such, but preferably the impurities are first removed or converted into harmless compounds and/or subjected to a treatment using micro-organisms in a biotreater.

HCN in the fat wash water may be hydrolysed by thermal decomposition at elevated temperature (150-250° C). $NH_3$ formed is decomposed in the biotreater in which for instance ferrous sulphate serves as a flocculant agent.

The synthesis gas mixture contains as major components carbon monoxide and hydrogen, and may contain further carbon dioxide, water, nitrogen, argon and minor amounts of compounds having 1-4 carbon atoms per molecule, such as methane, methanol and ethane. This gas mixture may be prepared by means of steam-/oxygen gasification of hydrocarbonaceous material, such as brown coal, anthracite, coke, crude mineral oils and fractions thereof, and oil recovered from tar sand and bituminous shale. Alternatively, this synthesis gas mixture may be obtained by steam methane reforming and/or catalytic partial oxidation of a hydrocarbonaceous material with an oxygen containing gas. Preferably natural gas is used as a feedstock for the preparation of the synthesis gas mixture. This gas mixture preferably has a hydrogen/carbon monoxide molar ratio higher than 1.5, preferably varying between about 1.75 to 2.25, most preferably is equal to about 2.0.

The synthesis gas mixture feed having an elevated temperature, e.g., a temperature of about 100-200° C. preferably, is cooled by indirect heat exchange in a gas cooler to about 15-75° C. and fed to a multi-stage gas scrubber washing zone which preferably is, in which the gaseous feed is successively washed with the bottom liquid of the scrubber, an aqueous solution containing ferrous sulphate and finally reaction water originating from the catalytic Fischer-Tropsch hydrocarbon synthesis reaction. Due to this washing treatment the final HCN and $NH_3$ content of the washed gas stream is lower than 0.1 ppm and is used in the Fischer-Tropsch synthesis reaction carried out at a temperature of 100-500° C., a total pressure of 1-200 bar abs. and a space velocity of 200-20,000 $m^3$ (STP) gaseous feed/$m^3$ reaction zone/hour. Preferred process conditions include a temperature of about 150-300° C., especially about 180-250° C., a pressure of 5-100 bar abs., preferably 15-30 bar, and a space velocity of 500-5,000 $m^3$ (STP) gaseous feed/$m^3$ reaction zone/hour. "STP" refers to a standard temperature (0° C.) and pressure (1 bar abs.). The reaction product is cooled and in a liquid separator water is separated from the hydrocarbons formed and is recycled to the gas scrubber.

The fat washing solution loaded with impurities (HCN and $NH_3$) is subjected to a thermal hydrolysis treatment at elevated temperature (100-200° C.) resulting in a decomposition of HCN. The treated solution is decontaminated in a biotreater using micro-organisms. If necessary, additional agents, such as flocculants and settling agents, may be added to the liquid to be treated in the biotreater.

What is claimed is:

1. Process for the preparation of hydrocarbons by a catalytic reaction of a mixture of carbon monoxide and hydrogen, comprising the steps of:
   (i) providing a gas mixture comprising carbon monoxide and hydrogen and at least one impurity selected from hydrogen cyanide and ammonia;
   (ii) washing in a wash zone said gas mixture in a first washing step using reaction water and a second washing step with an aqueous solution comprising chemicals promoting the absorption of the impurities; to obtain a washed gas mixture having a reduced level of impurities and a fat aqueous solution containing impurities from said gas mixture;
   (iii) separating said fat aqueous solution from the mixture;
   (iv) contacting said washed gas mixture at an elevated temperature and pressure with a catalyst whereby a hydrocarbon-containing reaction product and reaction water are obtained;
   (v) separating said reaction water from said hydrocarbon product; and
   (vi) recycling at least part of said reaction water solution to said wash zone of step (ii).

2. Process as in claim 1, wherein in step (ii) the chemicals in the second washing step are selected from the group consisting of iron sulphate and sodium hydroxide.

3. Process as in claim 1, wherein for the washing treatment of step (ii) the mixture of carbon monoxide and hydrogen has a temperature from 15-75° C.

4. Process as in claim 1, wherein at least part of the fat washing solution containing the impurities and separated from step (iii) is subjected to an elevated temperature between 150-250° C. to hydrolyze HCN therein.

5. In a Fischer-Tropsch process for the catalytic synthesis of hydrocarbons in a reaction zone from a feed mixture of carbon monoxide and hydrogen and at least one impurity selected from hydrogen cycanide and ammonia wherein the reaction product comprises water, the improvement comprising
   i) washing said feed gas mixture in a wash zone with an aqueous wash solution containing at least one chemical selected from ferrous sulfate and sodium hydroxide, to obtain a washed gaseous mixture having a reduced amount of said impurity and a fat wash solution containing at least some of the impurity removed from said gas feed mixture,
   ii) separating said fat wash solution from said washed gas mixture,
   iii) passing said washed gas mixture as feed to a reaction zone and contacting said feed with a Fischer-Tropsch catalyst to obtain a reaction product containing hydrocarbons and reaction water,
   iv) separating said reaction water from said hydrocarbons, and
   v) recycling at least part of said reaction water to said wash zone of step (i).

* * * * *